United States Patent

Komma et al.

[11] Patent Number: 5,308,391
[45] Date of Patent: May 3, 1994

[54] CERAMIC MATERIAL FOR VENEERING METALLIC DENTAL PROTHESES

[75] Inventors: Ottmar Komma, Niddatal; Juergen Steidl, Woellstadt, both of Fed. Rep. of Germany

[73] Assignee: Ducera Dental-Gesellschaft mbH, Rosbach, Fed. Rep. of Germany

[21] Appl. No.: 120,471

[22] Filed: Sep. 14, 1993

Related U.S. Application Data

[63] Continuation of Ser. No. 27,589, Mar. 5, 1993, abandoned, which is a continuation of Ser. No. 764,231, Sep. 23, 1991, abandoned.

[30] Foreign Application Priority Data

Oct. 3, 1990 [DE] Fed. Rep. of Germany ....... 4031168

[51] Int. Cl.$^5$ ..................... A61C 13/083; C03C 3/091
[52] U.S. Cl. ......................... 106/35; 501/59; 501/64; 501/66; 433/212.1
[58] Field of Search ........ 501/59, 66, 69, 70, 501/72, 64; 106/35; 433/212.1

[56] References Cited

U.S. PATENT DOCUMENTS

| | | | |
|---|---|---|---|
| 2,527,693 | 10/1950 | Armistead | 501/59 X |
| 4,349,692 | 9/1982 | Davis et al. | |
| 4,576,922 | 3/1986 | O'Brien et al. | 501/59 X |
| 4,619,810 | 12/1986 | Prasad | |
| 5,009,709 | 4/1991 | Ibsen et al. | 106/35 |

FOREIGN PATENT DOCUMENTS

| | | |
|---|---|---|
| 1251306 | 3/1989 | Canada . |
| 0159205 | 10/1985 | European Pat. Off. . |
| 0328772 | 8/1989 | European Pat. Off. . |
| 3911460 | 11/1990 | Fed. Rep. of Germany . |
| 955091 | 1/1950 | France . |

OTHER PUBLICATIONS

SU 908,355, English language abstract, World Patents Index Latest, Weel 8251, AN 82-11217J, Feb. 1982.
JP 63-156036, English language abstract, Patent Abstracts of Japan, vol. 12 No. 426, Nov. 10, 1988.
Scholze, H., "Glas, Natur, Struktur, Eigenschaften" ("Glass, Nature, Structure, Properties"), 1965, pp. 54–67; English language translation attached.

*Primary Examiner*—Karl Group
*Attorney, Agent, or Firm*—Beveridge, DeGrandi, Weilacher & Young

[57] ABSTRACT

Ceramic masses with processing temperatures of approximately 770° C. and coefficients of thermal expansion of $8\text{-}9\cdot10^{-6}$ $K^{-1}$ and $16\text{-}17.5\cdot10^{-6}$ $K^{-1}$ are required for dental prostheses consisting of low-melting gold alloys and titanium alloys for their veneering. Such ceramic masses are composed of 60 to 75% by weight $SiO_2$, 4 to 15% by weight $Al_2O_3$, 0.7 to 2.5% by weight $B_2O_3$, 0 to 0.9% by weight $Sb_2O_3$, 0 to 0.5% by weight $CeO_2$, 0 to 2.5% by weight $BaO$, 0 to 0.5% by weight $CaO$, 7 to 12% by weight $K_2O$, 6 to 11% by weight $Na_2O$, 0.55 to 1.4% by weight $Li_2O$ and 0.2 to 1.0% by weight $F_2$.

12 Claims, No Drawings

CERAMIC MATERIAL FOR VENEERING METALLIC DENTAL PROTHESES

This application is a continuation of application Ser. No. 08/027,589, filed Mar. 5, 1993, now abandoned, which application is entirely incorporated herein by reference, and is a continuation of application Ser. No. 07/764,231, filed Sep. 23, 1991, now abandoned, which application is entirely incorporated by reference.

INTRODUCTION AND BACKGROUND

The present invention relates to a ceramic material or veneering metallic dental prostheses formed of low-melting gold alloys or titanium with a processing temperature of 770° C. ±70° C. and with a coefficient of thermal expansion, a, between 20° and 500° C. of $8 \cdot 10^{-6} K^{-1}$ to $17.5 \cdot 10^{-6} K^{-1}$ which can be adjusted to be compatible with particular dental alloys.

Ceramic layers have been used as a veneer to form an enamelling of underlying metallic supporting frameworks (crowns, bridges) for many years in the field of dentistry in order to achieve a natural appearance of the dental prosthesis. For this, ceramic powders are applied as an aqueous slip onto the metallic framework and fired at high temperatures. It is important in carrying this out that the firing temperature (processing temperature) of the ceramic mass is at least 100° C. below the solidus temperature of the material of the metal framework. Also, it is important that the coefficient of thermal expansion of the ceramic mass in the range of 20° to 500° C. is slightly less than that of the metal material in order that no tears occur in the veneering layer during the firing operation and later during the cooling period.

Gold alloys with gold contents between 70 and 85% have recently been used in the field of dentistry which exhibit coefficients of thermal expansion between 16 and $17.5 \cdot 10^{-6} K^{-1}$. In addition, titanium materials are used with coefficients of thermal expansion between 9 and $10 \cdot 10^{-1} K^{-1}$. Moreover, these gold alloys exhibit solidus temperatures in a range of 870°–940° C. It is important in the case of titanium materials to remain below the phase transition temperature of approximately 880° C. during the firing operation.

Ceramic masses which cover such a broad range of the coefficient of thermal expansion and exhibit at the same time a processing temperature in a range of approximately 700°–840° C. have not been known in the past.

SUMMARY OF THE INVENTION

An object of the present invention is to provide a ceramic material capable of forming a strongly adhering veneer on the surface of dental prostheses made of low-melting gold alloys and titanium. A feature of the ceramic substances of this invention is that they exhibit a processing temperature of 770° C.±70° C. and a coefficient of thermal expansion between 20° and 500° C. which can be adjusted to values between $8 \cdot 10^{-6}$ and $17.5 \cdot 10^{-6} K^{-1}$, especially to values of $8-9 \cdot 10^{-6} K^{-1}$ and $16-17.5 \cdot 10^{-6} K^{-1}$.

The invention solves the problems of the prior art with a ceramic material composed of: 60–75% by weight $SiO_2$, 4–15% by weight $Al_2O_3$, 0.7–2.5% by weight $B_2O_3$, 0–0.9% by weight $Sb_2O_3$, 0–0.5% by weight $CeO_2$, 0–2.5% by weight $BaO$, 0–0.5% by weight $CaO$, 7–12% by weight $K_2O$, 6–11% by weight $Na_2O$, 0.55–1.4% by weight $Li_2O$ and 0.2–1.0% by weight $F_2$.

For gold alloys with coefficients of thermal expansion between 16 and $17.5 \cdot 10^{-6} K^{-1}$, ceramic materials with the following composition have proven themselves: 60–68% by weight $SiO_2$, 10–15% by weight $Al_2O_3$, 0.7–1.5% by weight $B_2O_3$, 0–0.5% by weight $Sb_2O_3$, 0–0.5 $CeO_2$, 0–0.5% by weight $BaO$, 0.1–0.5% by weight $CaO$, 9–12% by weight $K_2O$, 9–11% by weight $Na_2O$, 0.8–1.4% by weight $Li_2O$ and 0.2–0.4% by weight $F_2$.

The following compositions have proven themselves in particular: 62–65% by weight $SiO_2$, 12–15% by weight $Al_2O_3$, 0.8–1.2% by weight $B_2O_3$, 0–0.2% by weight $Sb_2O_3$, 0–0.4% by weight $CeO_2$, 0–0.1% by weight $BaO$, 0.2–0.4% by weight $CaO$, 9–12% by weight $K_2O$, 9–11% by weight $Na_2O$, 0.8–1.2% by weight $Li_2O$ and 0.2–0.4% by weight $F_2$.

Ceramic materials with the following compositions have proven themselves for titanium and titanium alloys with coefficients of thermal expansion of $9-10 \cdot 10^{-6} K^{-1}$: 68–75% by weight $SiO_2$, 4–8% by weight $Al_2O_3$, 2–2.5% by weight $B_2O_3$, 0.3–0.9% by weight $Sb_2O_3$, 0–0.2% by weight $CeO_2$, 0.5–2.5% by weight $BaO$, 0–0.3% by weight $CaO$, 7–11% by weight $K_2O$, 6–10% by weight $Na_2O$, 0.55–0.75% by weight $Li_2O$ and 0.8–1.0% by weight $F_2$.

Compositions with 70–74% by weight $SiO_2$, 4–7% by weight $Al_2O_3$, 2.1–2.4% by weight $B_2O_3$, 0.4–0.6% by weight $Sb_2O_3$, 1.8–2.2% by weight $BaO$, 0–0.1% by weight $CaO$, 7–9% by weight $K_2O$, 7–9% by weight $Na_2O$, 0.55–0.75% by weight $Li_2O$ and 0.8–1.0% by weight $F_2$ have proven themselves in particular.

All of these ceramic materials have a processing temperature in a range between 700° and 840° C. and can be adjusted to coefficients of expansion between $8 \cdot 10^{-6}$ and $17.5 \cdot 10^{-6} K^{-1}$ in the range between 20° and 500° C.

DETAILED DESCRIPTION OF THE INVENTION

The following examples are intended are explain the invention in more detail:

EXAMPLE 1

A yellow dental alloy consisting of 77% gold, 9% silver, 2% palladium, 4.3% platinum, 4.5% copper, 2% indium and 1.2% zinc with a solidus temperature of 900° C. and a coefficient of thermal expansion of $16.5 \cdot 10^{-6} K^{-1}$ was veneered with a ceramic mass with the composition 63.2% $SiO_2$, 12.8% $Al_2O_3$, 0.8% $B_2O_3$, 0.2% $Sb_2O_3$, 0.2% $CeO_2$, 0.1% $BaO$, 0.3% $CaO$, 10.6% $K_2O$, 10.4% by weight $Na_2O$, 1.1% $Li_2O$ and 0.3% fluoride at 770° C.

The ceramic mass exhibited a dilatometric softening point of 550° C., a glass point of 460° C. and a coefficient of thermal expansion of $16.2 \cdot 10^{-6} K^{-1}$.

After being fired on, the ceramic mass exhibited a very good surface structure which was above the usual level of the known ceramics whereas the transparency was comparable with these masses.

The shearing test according to the pattern of DIN 13927 is 34 N/nm². This value is in the average range in comparison to other fired-on alloys and normal metallic ceramic masses.

The composite test (qualitative adhesion test) according to ISO 9693.2 and pattern DIN 13927 is passed in a superb manner.

The hydrolysis resistance—boiled 16 hours in 4% acetic acid according to ISO 9693.2 and DIN 13925 and pattern DIN 13927—yielded practically no weighable loss of mass. The sheen condition of the test specimen is practically unchanged.

The flexural resistance according to DIN 13925 and ISO 9693.2 is about 75 N/mm² and thus approximately 50% above the minimum flexural resistance of 50 N/mm² required according to DIN and ISO.

EXAMPLE 2

A titanium bridge framework with a coefficient of thermal expansion of $9.6 \cdot 10^{-6} K^{-1}$ was veneered with a ceramic mass with the composition 72.5% by weight $SiO_2$, 4.5% by weight $Al_2O_3$, 2.5% by weight $B_2O_3$, 0.3% by weight $Sb_2O_3$, 2.2% by weight Bao, 7.5% by weight $K_2O$, 9.0% by weight $Na_2O$, 0.7% by weight $Li_2O$ and 0.8% by weight fluoride at 720° C.

The ceramic mass exhibits a dilatometric softening point of 570° C., a glass point of 480° C. and a coefficient of thermal expansion of $8.3 \times 10^{-6} K^{-1}$.

After having been fired, the transparency as well as the surface structure of the ceramic masses were surprisingly good and were above the usual level of the normal metallic ceramic masses. The shearing test according to procedure DIN 13927 was 30 N/mm² on the average.

The composite test (qualitative adhesion test) according to ISO 9693.2 and procedure DIN 13927 was passed superbly. The hydrolysis resistance, boiled 16 hours in 4% acetic acid according to ISO 9693.2 and DIN 13925 and procedure DIN 13927, yielded practically no weighable loss of mass. The sheen condition of the test specimen was practically unchanged. The flexural resistance according to DIN 13925 and ISO 9693.2 was about 85 N/mm² and thus approximately 70% above the minimum flexural resistance of 50 N/mm² required according to DIN and ISO.

The ceramic compositions of the present invention can be used to form veneer over metallic dental structures that form the underlying bodies for dentures such as crowns and bridgework. This is carried out by coating the metallic member and then firing at the suitable temperature and for a sufficient period of time. Further variations and modifications of the foregoing will be apparent to those skilled in the art and are intended to be encompassed by the appended claims.

German priority application P 40 31 168.6 is relied on and incorporated herein by reference.

We claim:

1. A method of using a ceramic material to make a veneer on a gold alloy dental prostheses comprising depositing a ceramic material on said gold alloy dental prostheses and firing at a sufficiently high temperature and for a sufficient period of time to form said veneer, said ceramic material having a coefficient of thermal expansion between 20° and 500° C. of $16 \cdot 10^{-6}$ to $17.5 \cdot 10^{-6} K^{-1}$ and comprising 60 to 68% by weight $SiO_2$, 10 to 15% by weight $Al_2O_3$, 0.7 to 1.5% by weight $B_2O_3$, 0 to 0.5% by weight $Sb_2O_3$, 0 to 0.5% by weight $CeO_2$, 0 to 0.5% by weight BaO, 0.1 to 0.5% by weight CaO, 9 to 12% by weight $K_2O$, 9 to 11% by weight $Na_2O$, 0.8 to 1.4% by weight $Li_2O$ and 0.2 to 0.4% by weight $F_2$ and wherein said gold alloy dental prothesis comprises a gold alloy having a coefficient of thermal expansion between 20° and 500° C. of $16 \cdot 10^{-6}$ to $17.5 \cdot 10^{-6} K^{-1}$.

2. The method according to claim 1, wherein said ceramic material veneer comprises 62 to 65% by weight $SiO_2$, 12 to 15% by weight $Al_2O_3$, 0.8 to 1.2% by weight $B_2O_3$, 0 to 0.2% by weight $Sb_2O_3$, 0 to 0.4% by weight $CeO_2$, 0 to 0.1% by weight BaO, 0.2 to 0.4% by weight CaO, 9 to 12% by weight $K_2O$, 9 to 11% by weight $Na_2O$, 0.8 to 1.2% by weight $Li_2O$ and 0.2 to 0.4% by weight $F_2$.

3. The method according to claim 1, wherein said ceramic material veneer comprises 63.2% by weight $SiO_2$, 12.8% by weight $Al_2O_3$, 0.8% by weight $B_2O_3$, 0.2% by weight $Sb_2O_3$, 0.2% by weight $CeO_2$, 0.1% by weight BaO, 0.3% by weight CaO, 10.6% by weight $K_2O$, 10.4% by weight $Na_2O$, 1.1% by weight $Li_2O$, and 0.3% by weight $F_2$ and has a coefficient of thermal expansion of $16.2 \cdot 10^{-6} K^{-1}$.

4. A method of using a ceramic material to make a veneer on a titanium or titanium alloy dental prostheses comprising depositing a ceramic material on said titanium or titanium alloy dental prostheses and firing at a sufficiently high temperature and for a sufficient period of time to form said veneer, said ceramic material having a coefficient of thermal expansion between 20° and 500° C. of $8 \cdot 10^{-6}$ to $17.5 \cdot 10^{-6} K^{-1}$ and comprising 68 to 75% by weight $SiO_2$, 4 to 8% by weight $Al_2O_3$, 2 to 2.5% by weight $B_2O_3$, 0.3 to 0.9% by weight $Sb_2O_3$, 0 to 0.2% by weight $CeO_2$, 0.5 to 2.5% by weight BaO, 0 to 0.3% by weight CaO, 7 to 11% by weight $K_2O$, 6 to 10% by weight $Na_2O$, 0.55 to 0.75% by weight $Li_2O$ and 0.8 to 1.0% by weight $F_2$.

5. The method according to claim 4, wherein said ceramic material veneer comprises 70 to 74% by weight $SiO_2$, 4 to 7% by weight $Al_2O_3$, 2.1 to 2.4% by weight $B_2O_3$, 0.4 to 0.6% by weight $Sb_2O_3$, 1.8 to 2.2% by weight BaO, 0 to 0.1% by weight CaO, 7 to 9% by weight $K_2O$, 7 to 9% by weight $Na_2O$, 0.55 to 0.75% by weight $Li_2O$ and 0.8 to 1.0% by weight $F_2$.

6. The method according to claim 4, wherein said ceramic material veneer comprises 72.5% by weight $SiO_2$, 4.5% by weight $Al_2O_3$, 2.5% by weight $B_2O_3$, 0.3% by weight $Sb_2O_3$, 2.2% by weight BaO, 7.5% by weight $K_2O$, 9.0% by weight $Na_2O$, 0.7% by weight $Li_2O$ and 0.8% by weight $F_2$ and has a coefficient of thermal expansion of $8.3 \cdot 10^{-6} K^{-1}$.

7. A veneered dental prothesis comprising a ceramic material veneer and a dental prothesis, wherein said dental prothesis comprises a gold alloy having a coefficient of thermal expansion between 20° and 500° C. of $16 \cdot 10^{-6}$ to $17.5 \cdot 10^{-6} K^{-1}$ and said ceramic material veneer has a coefficient of thermal expansion between 20° and 500° C. of $16 \cdot 10^{-6}$ to $17.5 \cdot 10^{-6} K^{-1}$ and comprises 60 to 68% by weight $SiO_2$, 10 to 15% by weight $Al_2O_3$, 0.7 to 1.5% by weight $B_2O_3$, 0 to 0.5% by weight $Sb_2O_3$, 0 to 0.5% by weight $CeO_2$, 0 to 0.5% by weight BaO, 0.1 to 0.5% by weight CaO, 9 to 12% by weight $K_2O$ and 0.2 to 0.4% by weight $F_2$.

8. The veneered dental prothesis according to claim 7, wherein said ceramic material veneer comprises 62 to 65% by weight $SiO_2$, 12 to 15% by weight $Al_2O_3$, 0.8 to 1.2% by weight $B_2O_3$, 0 to 0.2% by weight $Sb_2O_3$, 0 to 0.4% by weight $CeO_2$, 0 to 0.1% by weight BaO, 0.2 to 0.4% by weight CaO, 9 to 12% by weight $K_2O$, 9 to 11% by weight $Na_2O$, 0.8 to 1.2% by weight $Li_2O$ and 0.2 to 0.4% by weight $F_2$.

9. The veneered dental prothesis according to claim 7, wherein said ceramic material veneer comprises 63.2% by weight $SiO_2$, 12.8% by weight $Al_2O_3$, 0.8% by weight $B_2O_3$, 0.2% by weight $Sb_2O_3$, 0.2% by weight CeO$_2$, 0.1% by weight BaO, 0.3% by weight CaO, 10.6% by weight K$_2$O, 10.4% by weight Na$_2$O, 1.1% by weight Li$_2$O and 0.3% by weight F$_2$ and has a coefficient of thermal expansion of $16.2 \cdot 10^{-6}$ K$^{-1}$.

10. A veneered dental prothesis comprising a ceramic material veneer and a dental prothesis, wherein said dental prothesis comprises titanium or a titanium alloy having a coefficient of thermal expansion between 20° and 500° C. of $9 \cdot 10^{-6}$ to $10 \cdot 10^{-6}$ K$^{-1}$ and said ceramic material veneer has a coefficient of thermal expansion between 20° and 500° C. of $8 \cdot 10^{-6}$ to $9 \cdot 10^{-6}$ K$^{-1}$ and comprises 68 to 75% by weight SiO$_2$, 4 to 8% by weight Al$_2$O$_3$, 2 to 2.5% by weight B$_2$O$_3$, 0.3 to 0.9% by weight Sb$_2$O$_3$, 0 to 0.2% by weight CeO$_2$, 1.5 to 2.5% by weight BaO, 0 to 0.3% by weight CaO, 7 to 11% by weight K$_2$O, 6 to 10% by weight Na$_2$O, 0.55 to 0.75% by weight Li$_2$O and 0.8 to 1.0% by weight F$_2$.

11. The veneered dental prothesis according to claim 10, wherein said ceramic material veneer comprises 70 to 74% by weight SiO$_2$, 4 to 7% by weight Al$_2$O$_3$, 2.1 to 2.4% by weight B$_2$O$_3$, 0.4 to 0.6% by weight Sb$_2$O$_3$, 1.8 to 2.2% by weight BaO, 0 to 0.1% by weight CaO, 7 to 9% by weight K$_2$O, 7 to 9% by weight Na$_2$O, 0.55 to 0.75% by weight Li$_2$O and 0.8 to 1.0% by weight F$_2$.

12. The veneered dental prothesis according to claim 10, wherein said ceramic material veneer comprises 72.5% by weight SiO$_2$, 4.5% by weight Al$_2$O$_3$, 2.5% by weight B$_2$O$_3$, 0.3% by weight Sb$_2$O$_3$, 2.2% by weight BaO, 7.5% by weight K$_2$O, 9.0% by weight Na$_2$O, 0.7% by weight Li$_2$O and 0.8% by weight F$_2$ and has a coefficient of thermal expansion of $8.3 \cdot 10^{-6}$ K$^{-1}$.

* * * * *